(12) United States Patent
Kilbey et al.

(10) Patent No.: US 7,694,816 B2
(45) Date of Patent: Apr. 13, 2010

(54) DISPENSER SYSTEM WITH SEAL ON SLIDING DOOR

(76) Inventors: Bryan E. Kilbey, 590 Circle Dr., DeFuniak Springs, FL (US) 32435; Bruce Parker, 1121 Linganore Pl., Charlotte, NC (US) 28203

(*) Notice: Subject to any disclaimer, the term of this patent is extended or adjusted under 35 U.S.C. 154(b) by 412 days.

(21) Appl. No.: 11/650,091

(22) Filed: Jan. 5, 2007

(65) Prior Publication Data
US 2008/0164172 A1  Jul. 10, 2008

(51) Int. Cl.
*A61B 17/06* (2006.01)
(52) U.S. Cl. .................. 206/440; 206/53; 206/409; 220/212
(58) Field of Classification Search .......... 206/389, 206/397, 53–55, 403–407, 409–411, 438, 206/440, 441, 468; 220/212, 345.1–345.3, 220/756; 221/2, 33, 45; 602/6, 8, 48, 50
See application file for complete search history.

(56) References Cited

U.S. PATENT DOCUMENTS

| | | | | |
|---|---|---|---|---|
| 4,688,023 A | * | 8/1987 | McGill et al. ............ 220/345.4 |
| 5,003,970 A | * | 4/1991 | Parker et al. .................. 602/50 |
| 5,505,305 A | * | 4/1996 | Scholz et al. ................ 206/438 |
| 6,290,663 B1 | * | 9/2001 | Darcey .......................... 602/8 |
| 6,296,284 B1 | * | 10/2001 | Weischedel .............. 220/345.3 |
| 6,719,710 B2 | * | 4/2004 | Darcey .......................... 602/8 |
| 6,974,430 B2 | * | 12/2005 | Evans ............................ 602/8 |
| 6,981,590 B1 | * | 1/2006 | Ubel et al. .................. 206/440 |

* cited by examiner

*Primary Examiner*—Luan K Bui
(74) *Attorney, Agent, or Firm*—J. Wiley Horton

(57) ABSTRACT

A dispenser system having an integral sealing mechanism for resealing a severed end of a moisture-activated medical bandaging product. A sliding door closes the front of the dispenser system. The sliding door is raised and lowered by a handle preferably having a mechanical advantage. When raised, the sliding door's lower extreme defines a dispensing opening with the bottom of the box. A length of medical bandaging product can be pulled through this opening. When a user closes the door, the door's bottom extreme forms a tang and clevis interface which pinches the sleeve of the medical bandaging product and thereby form a moisture proof seal.

21 Claims, 16 Drawing Sheets

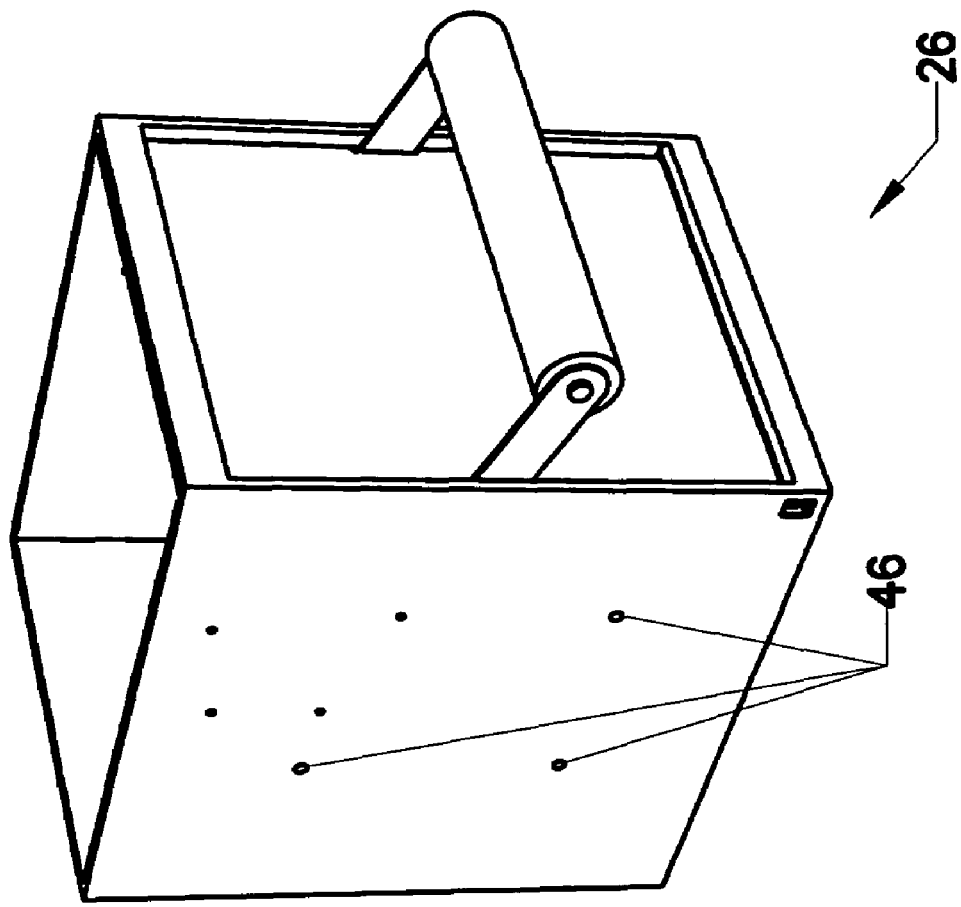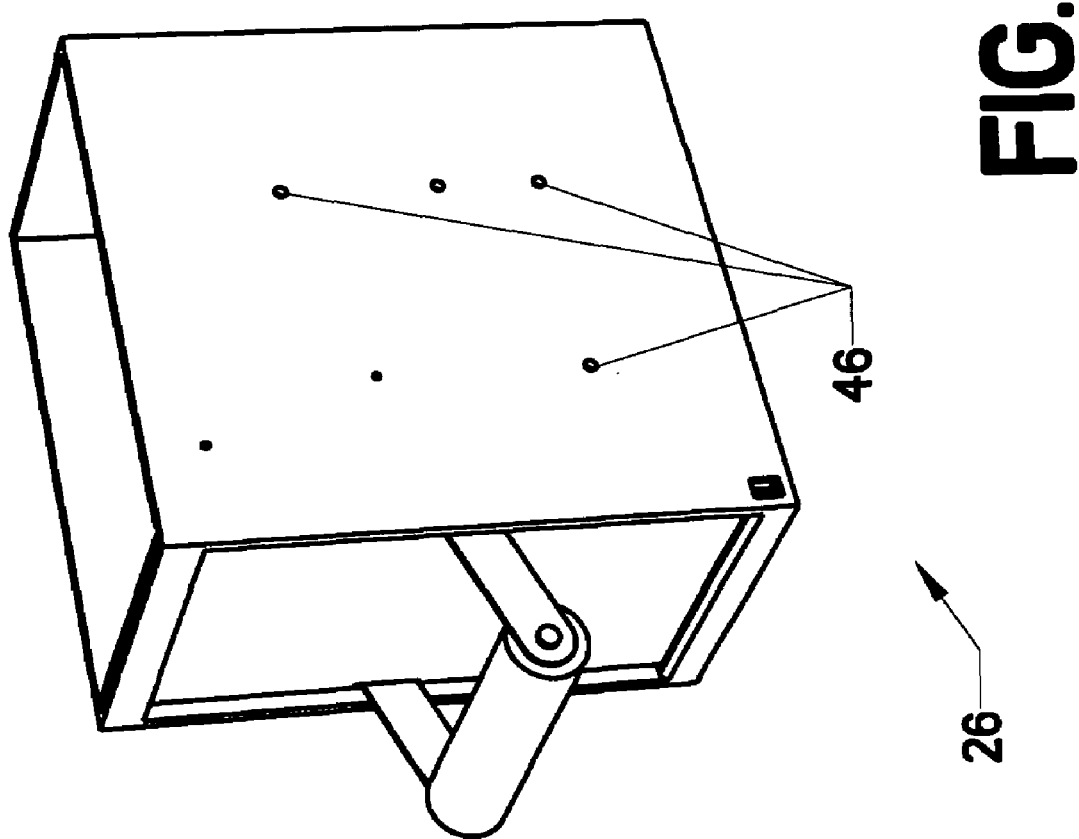
FIG. 12

DISPENSER SYSTEM WITH SEAL ON SLIDING DOOR

BACKGROUND OF THE INVENTION

1. Field of the Invention

This invention relates to the field of medical products. More specifically, the invention comprises a dispenser configured to dispense a medical bandaging product which must be cut and resealed.

2. Description of the Related Art

Orthopedic injuries have traditionally been treated by setting and immobilizing the affected region. Plaster-of-Paris casts served this role for many decades. Beginning in the 1980's, however, more advanced materials arrived. Most "casts" are now made of a composite fibrous material including a moisture-curable resin. The material is cut to length, infused with water, and wrapped around a desired portion of the patient's anatomy. The moisture then activates the resin and the composite material hardens in place. This process is disclosed in detail in U.S. Pat. Nos. 4,770,299; 4,869,046; 4,899,738; and 5,003,970 to A. Bruce Parker. These four patents are hereby incorporated by reference.

The composite fibrous material is customarily sealed in an elongated sleeve. FIG. 1 shows this arrangement, with the sleeve being designated as outer elongate sleeve 13. The composite fibrous material is designated as medical material 14. The elongate outer sleeve is sealed along its two parallel edges by a heat seal 16. The two ends are also sealed when the product is shipped from the manufacturing facility. The completed and sealed assembly is referred to as medical bandaging product 10.

Health care professionals in a variety of specialties customarily keep a substantial supply of medical bandaging product 10 on hand. FIG. 2 shows how it is typically stored. Since medical bandaging product 10 is long and thin, it is wrapped into a roll and placed within a dispenser 11. Medical bandaging product 10 is manufactured in a variety of widths in order to accommodate varying splint applications. Accordingly, the dispensers are made in a variety of widths.

Each dispenser opens into a slot 12, through which a medical technician can pull a desired length of medical bandaging product 10. The technician pulls out the desired length, then uses a pair of scissors or other cutting implement to sever the desired length from the roll. If the severed end of the roll is left open, atmospheric moisture will invade the outer elongate sleeve and cause the medical material to harden. Thus, the severed end of the roll must be resealed. A perfect seal is desired, since even slight permeability will cause the medical material to harden.

Foil tape has been used to reseal the opening, but this is rather cumbersome to use. FIG. 3 shows another solution which is known in the prior art. Clamp 18 is two separate members—tang 24 and clevis 22—pivotally connected by hinge 20. The two separate members rotate together to clamp the open end of medical bandaging product 10. FIG. 4 shows the interface between the two members in more detail. Tang 24 rotates down into clevis 22 and deforms outer elongate sleeve 13 of medical bandaging product 10 into the "U" shape shown. The result is an effective seal.

The clamp of FIGS. 3 and 4 has gained widespread acceptance, since it does effectively seal the outer elongate sleeve and eliminates the problem of moisture penetration. However, the clamp does have several drawbacks. First, because it is separate from the dispenser, it may be lost. Second, it can be difficult to open and close. This is particularly true for users with small hands, who may find prying the tang out of the clevis to be difficult. Thus, an improved sealing device is desired.

BRIEF SUMMARY OF THE PRESENT INVENTION

The present invention comprises a dispenser system having an integral sealing mechanism for resealing a severed or open portion of a medical bandaging product. The dispenser system receives a prior art dispenser containing a roll of medical bandaging product, which typically comprises a composite bandaging material located within an outer elongate seal made of foil. A sliding door closes the front of the dispenser system. The sliding door is raised and lowered by a handle preferably having a mechanical advantage. When raised, the sliding door's lower extreme defines a dispensing opening with the bottom of the box. A length of medical bandaging product can be pulled through this opening.

The user cuts the desired length of bandaging product free from the roll contained within the dispenser system. The user then pushes the composite bandaging material back down inside the outer foil seal so that the composite bandaging material rests within the dispenser system, while the outer foil seal protrudes through the dispensing opening. The user then pushes down on the handle to close the door. The door's bottom extreme forms a tang and clevis joint when closed. A portion of the medical bandaging product's outer foil sleeve is pinched within the tang and clevis joint thus formed, which creates a tight seal. Thus, by simply closing the sliding door, the user reseals the medical bandaging product.

BRIEF DESCRIPTION OF THE SEVERAL VIEWS OF THE DRAWINGS

FIG. 12 is a perspective view, showing two dispenser systems of differing widths.

REFERENCE NUMERALS IN THE DRAWINGS

| 10 | medical bandaging product | 11 | dispenser |
|---|---|---|---|
| 12 | slot | 13 | outer elongate sleeve |
| 14 | medical material | 15 | 6 inch box |
| 16 | heat seal | 18 | clamp |
| 20 | hinge | 22 | clevis |
| 24 | tang | 26 | dispenser system |
| 28 | top opening | 30 | left side wall |
| 32 | rear wall | 34 | right side wall |
| 36 | front wall | 38 | sliding door |
| 40 | handle | 42 | lever |
| 44 | pivot joint | 46 | mounting hole |
| 48 | front opening | 50 | right groove |
| 52 | left groove | 54 | indicator panel |
| 56 | lever relief | 58 | tang |
| 60 | insert | 62 | clevis |
| 64 | dispensing opening | 66 | 3 inch box |
| 68 | 4 inch box | 70 | opening |
| 72 | occluding panel | 74 | cutting device mount |
| 76 | water dispenser mount | 78 | bottle holder |
| 80 | water bottle | 82 | scissors |
| 84 | measuring tape | | |

DETAILED DESCRIPTION OF THE INVENTION

Figure 1:
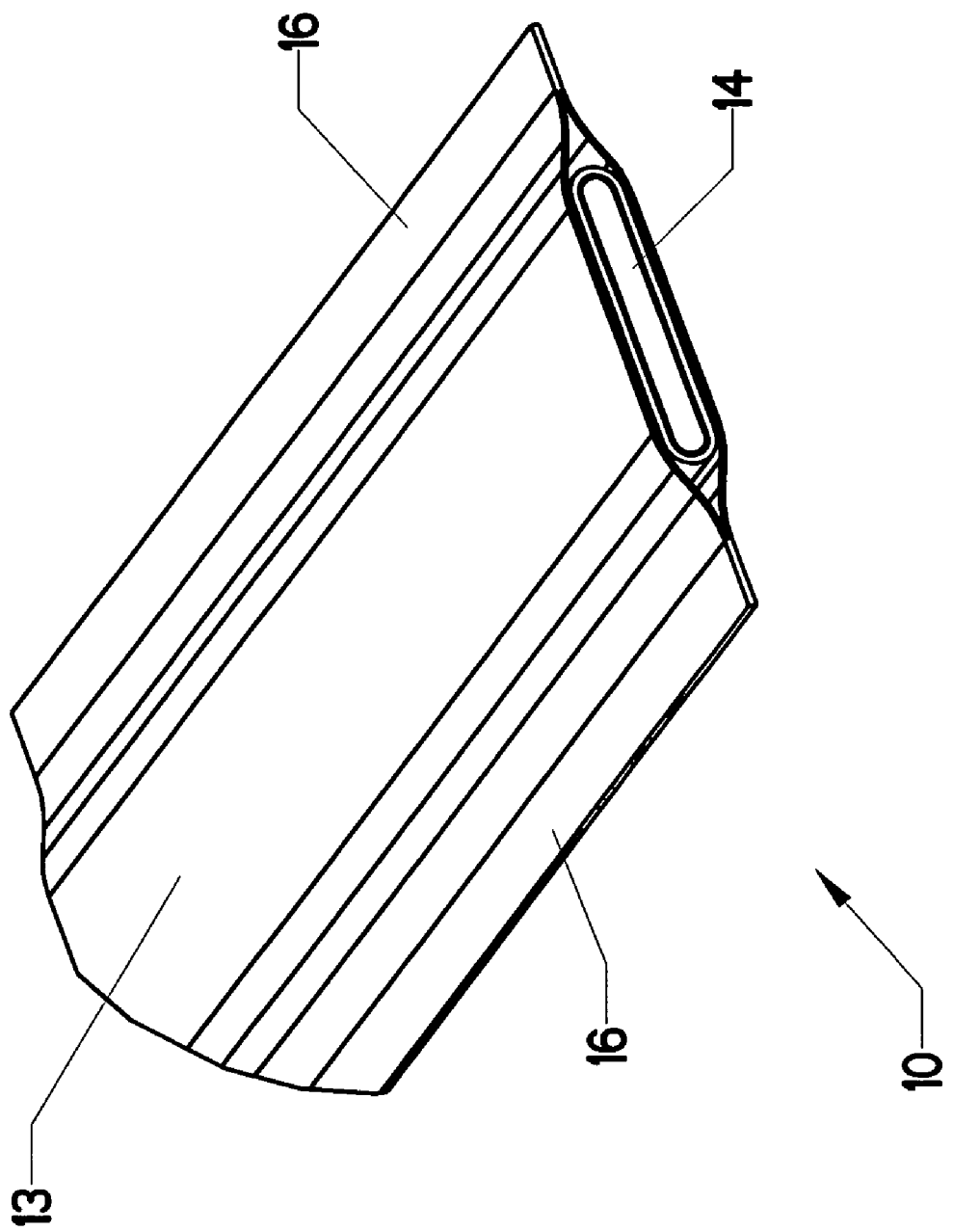
FIG. 1 is a perspective view showing the construction of a prior art medical bandaging product.
Figure 2:
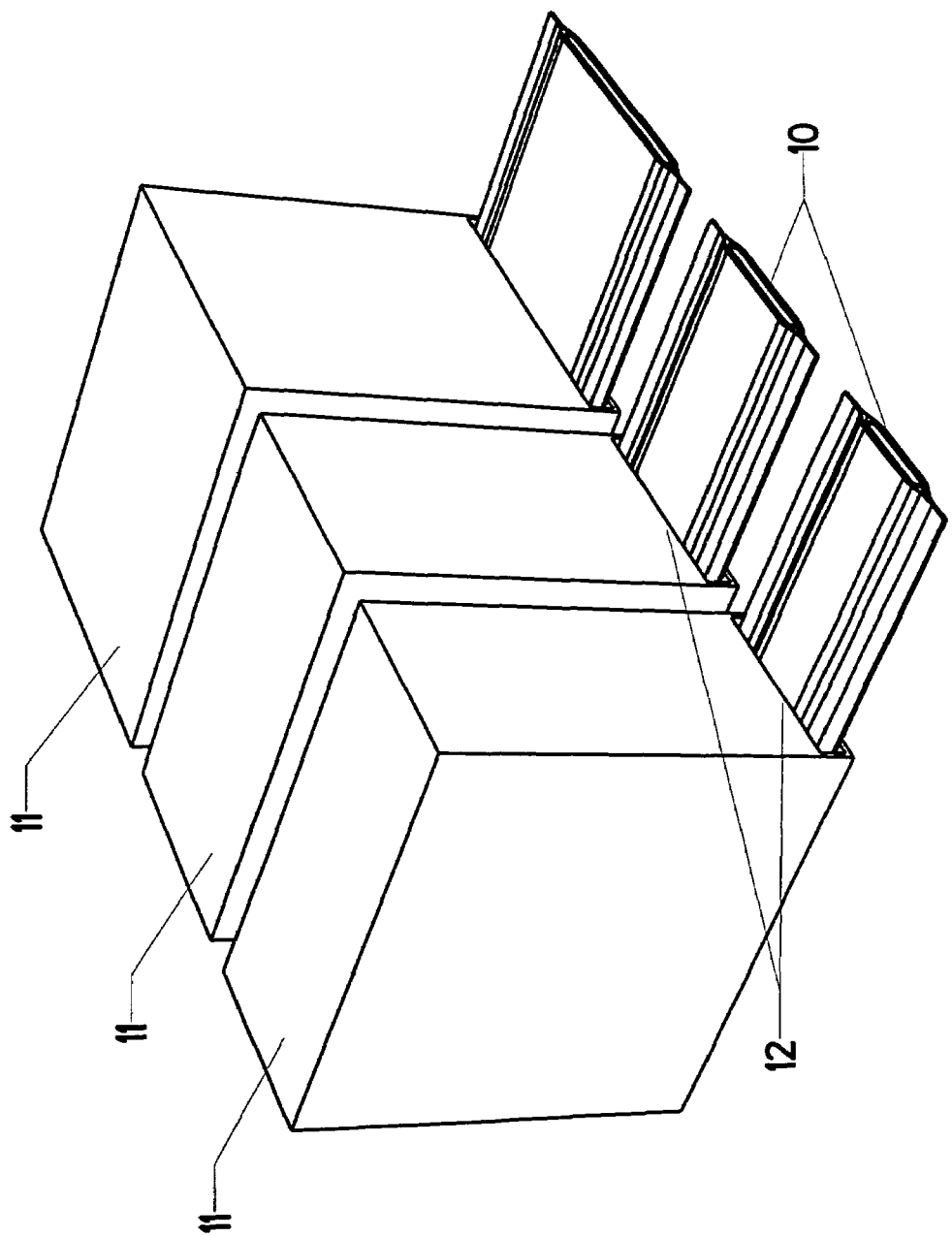
FIG. 2 is a perspective view, showing a group of prior art cardboard dispensers.
Figure 3:
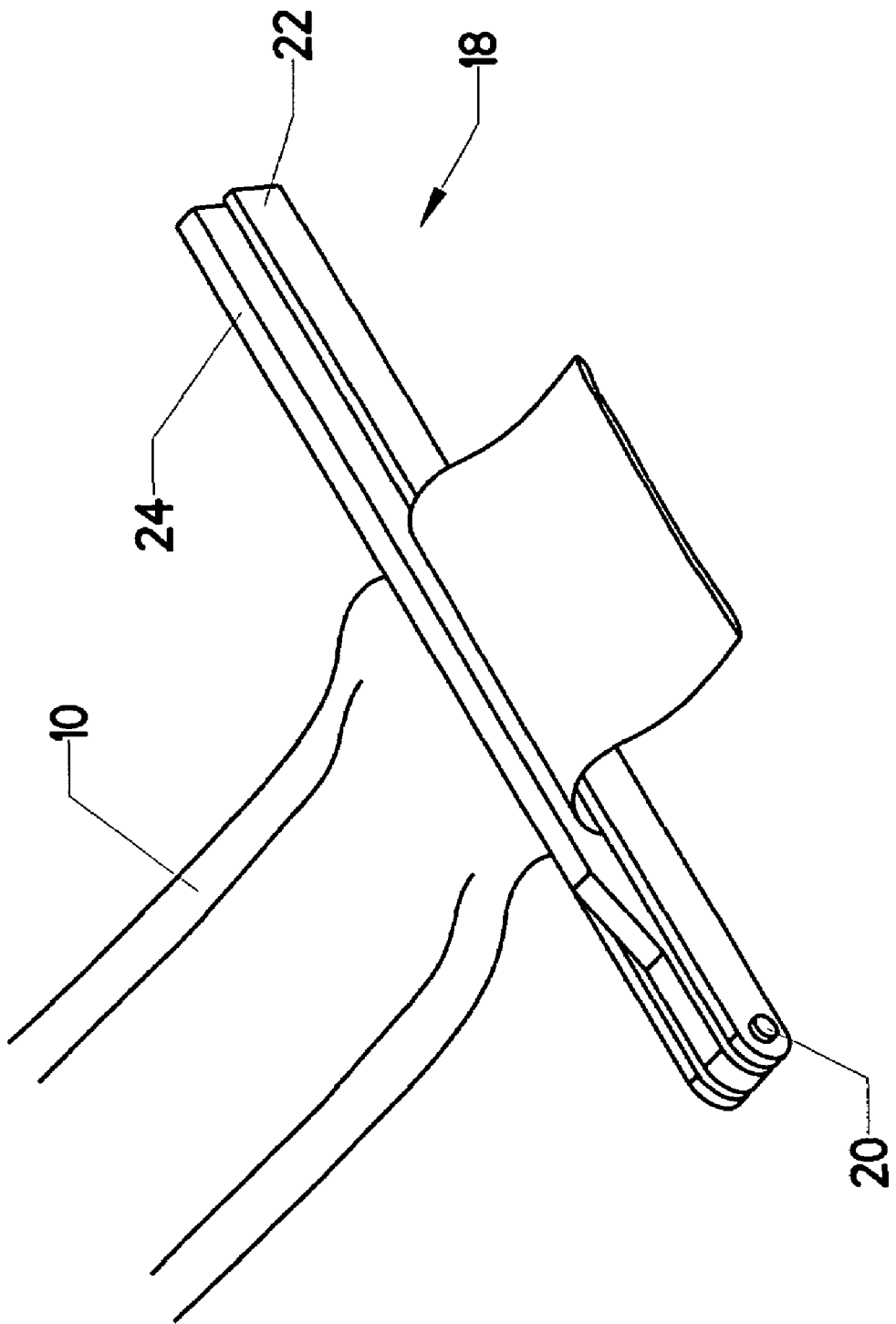
FIG. 3 is a perspective view, showing a prior art resealing clamp.
Figure 4:
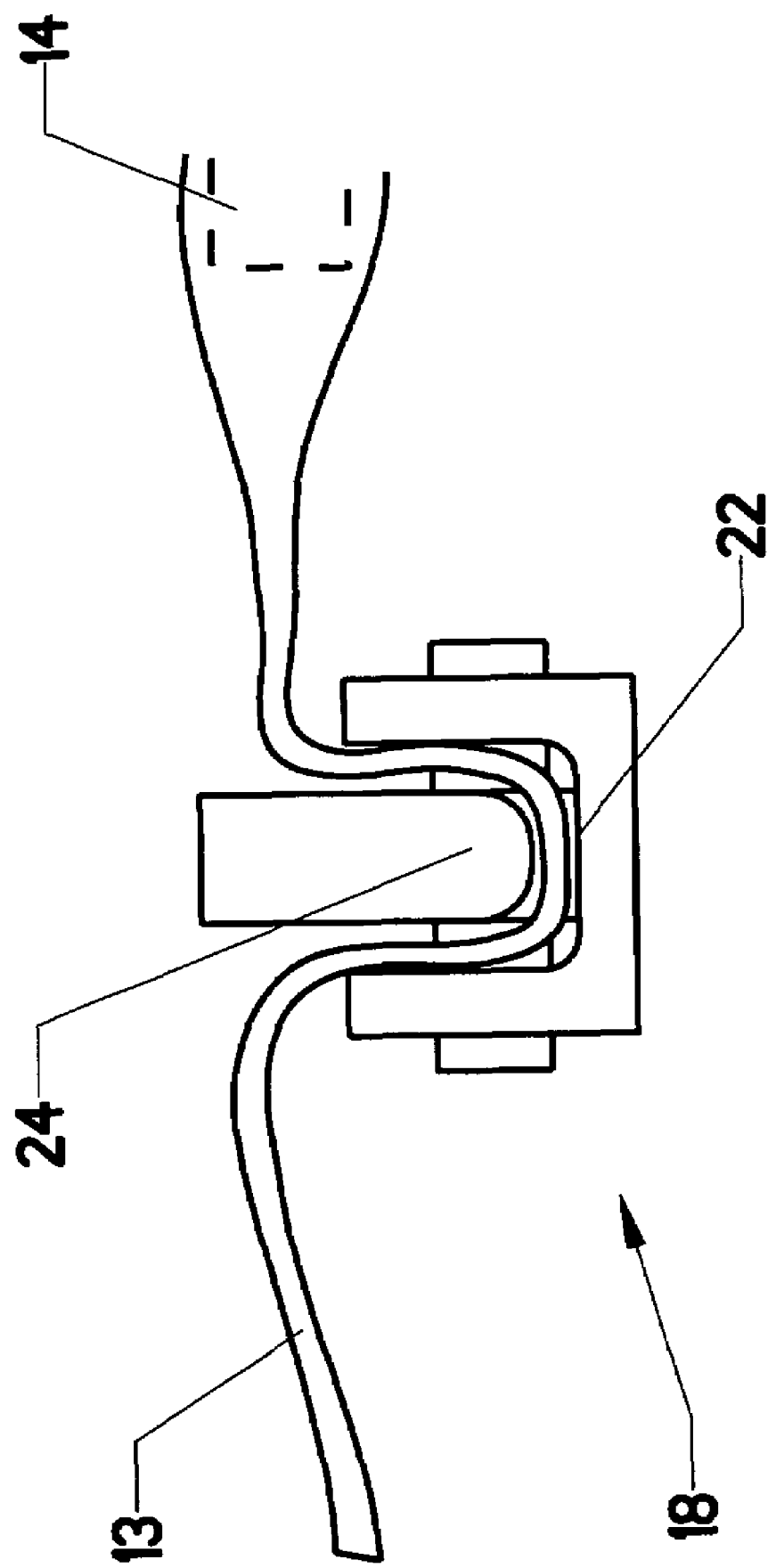
FIG. 4 is a sectional elevation view, showing the prior art clamp in use.
Figure 5:
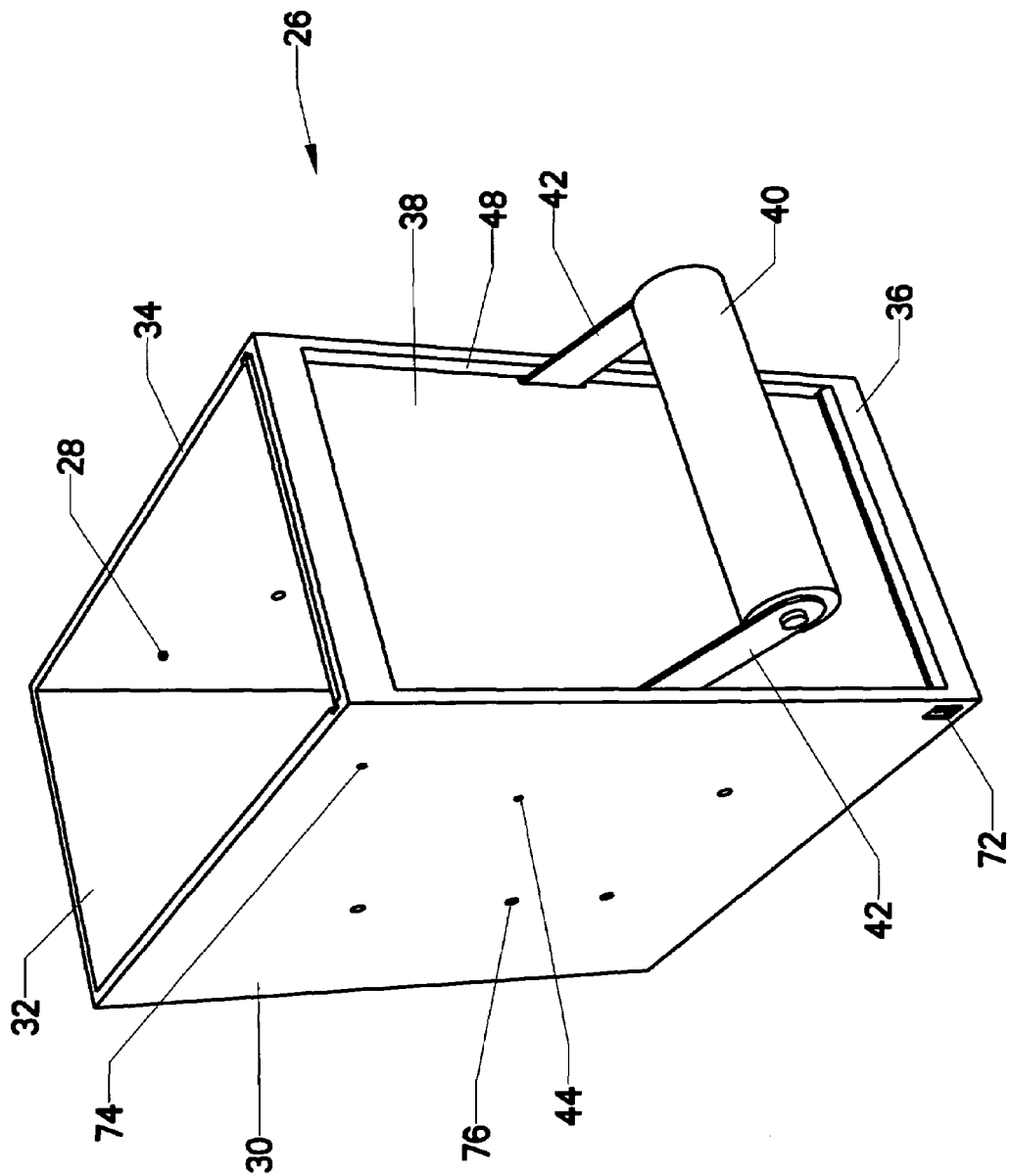
FIG. 5 is a perspective view, showing the present invention.

FIG. 5 shows a preferred embodiment of the present invention. Dispenser system 26 includes an enclosure formed by left side wall 30, right side wall 34, front wall 36, and rear wall 32 (A bottom is also included, though this is not shown). The front wall includes front opening 48. Sliding door 38 resides within the front opening. Pulling up or down on handle 40 causes the sliding door to raise or lower, as will be subsequently explained. Top opening 28 allows a container of medical material to be loaded into the dispenser system.

Handle 40 is attached to sliding door 38 by a pair of levers 42. The two levers actually pass through slots in the sliding door and attach to the sides of the enclosure at a pair of pivot joints 44 (only one pivot joint is visible in the view).

Figure 6:
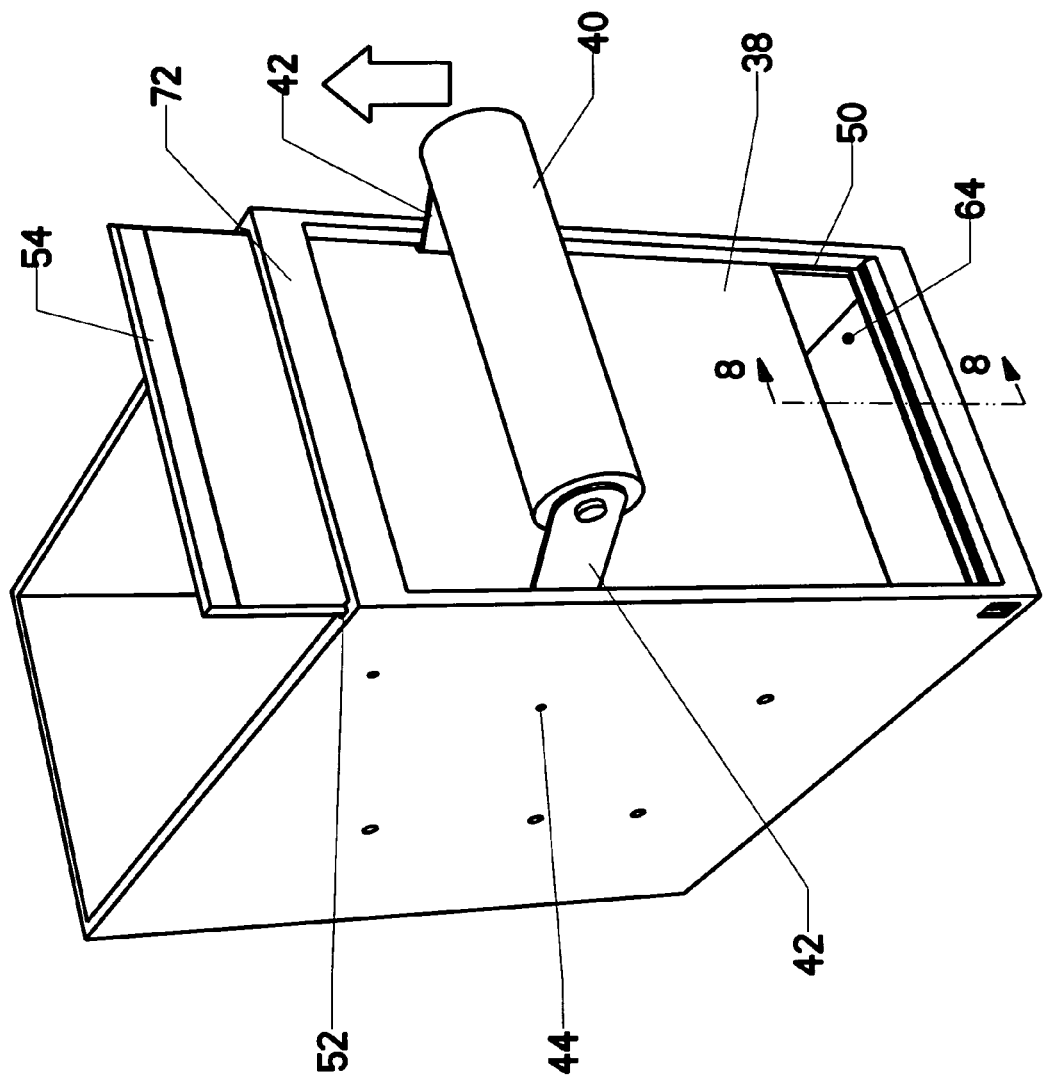
FIG. 6 is a perspective view, showing the present invention with the sliding door in a raised position.
Figure 7:
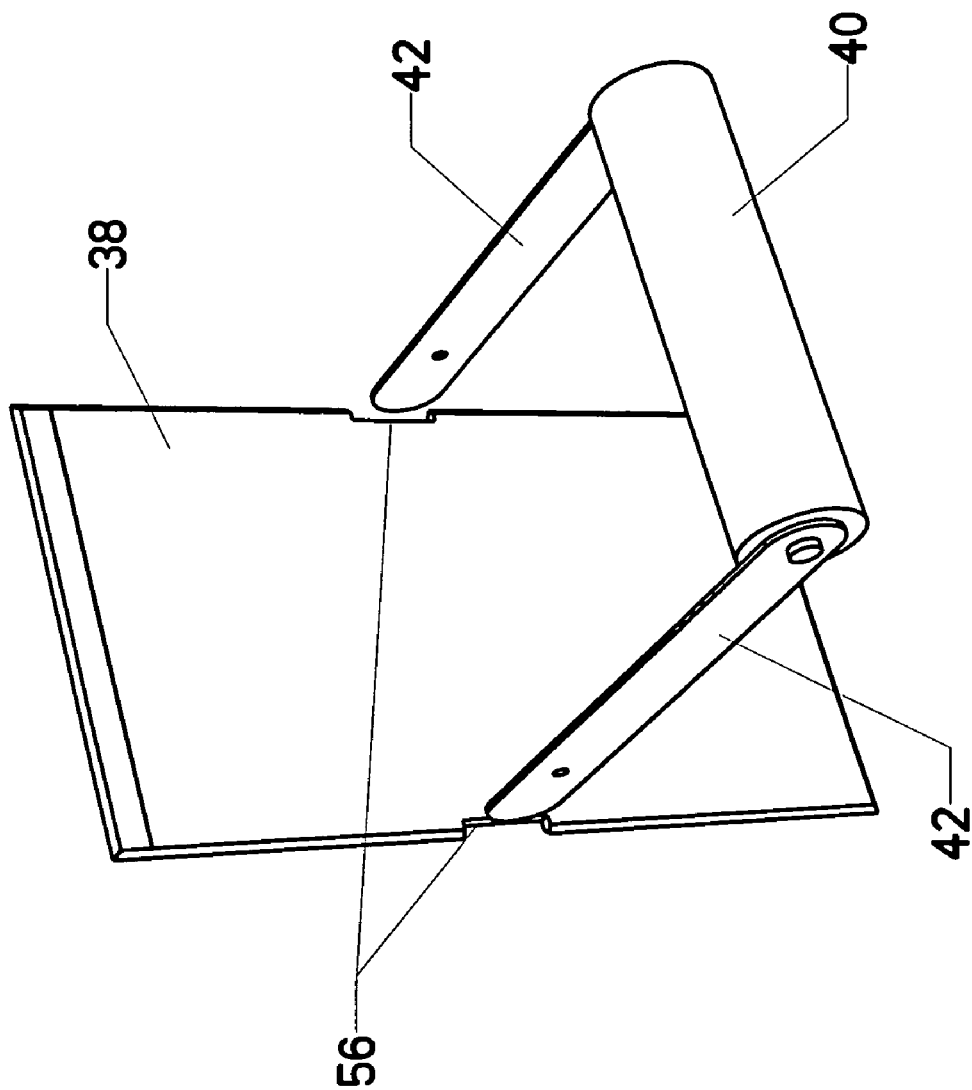
FIG. 7 is an exploded perspective view, showing the sliding door and handle.

In FIG. 6, handle 40 has been pulled upward. This action has caused sliding door 38 to move upward. Turning briefly to FIG. 7, the reader will observe that sliding door 38 includes a pair of lever reliefs 56. Levers 42 fit within these reliefs and pivotally attach to the enclosure. Thus, those skilled in the art will realize that if handle 40 is urged upward or downward, the two levers will bear against the boundaries of the two lever reliefs and move the sliding door upward or downward.

Those skilled in the art will also realize that the lever arrangement provides a mechanical advantage. The force applied to the sliding door will be a multiple of the force applied to the handle. Thus, a relatively weak user will still be able to generate sufficient closing force on the door. It is preferable to provide the handle with a soft and pliable gripping cover so that the user's hand is not fatigued.

Returning now to FIG. 6, the reader will observe that the enclosure includes right groove 50 and left groove 52. The right side of the sliding door slides within the right groove and the left side of the sliding door slides within the left groove. Handle 40 has been pulled upward in the view and the sliding door has thereby been raised. Dispensing opening 64 has thereby been created between the sliding door's lower extreme and the container. A length of medical bandaging product can be pulled through this dispensing opening—as will be seen.

Figure 8:
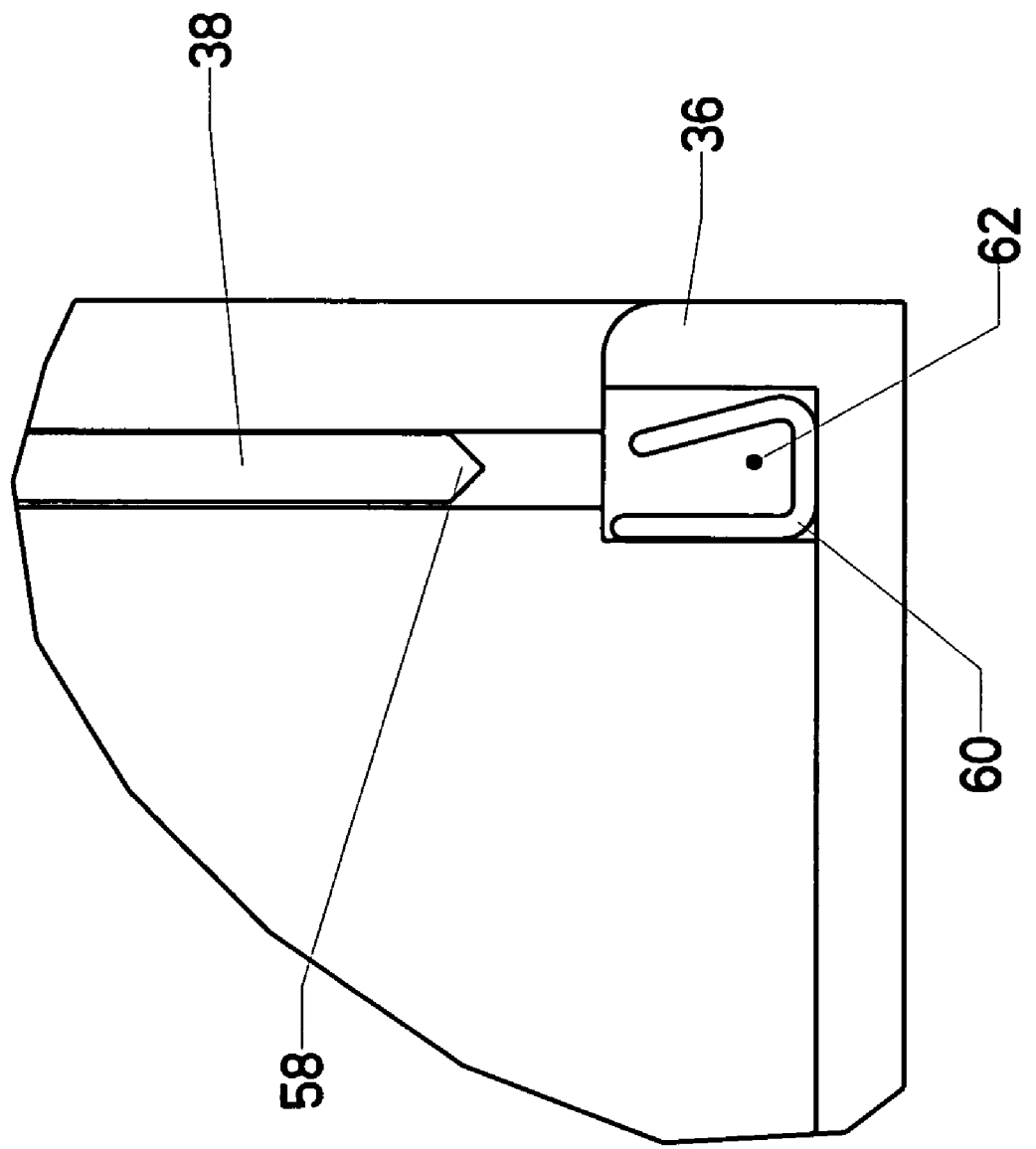
FIG. 8 is a sectional elevation view, showing the formation of a tang and clevis joint when the sliding door is closed.

It is important to the present invention that the lower extreme of the sliding door provide a good seal when the door is closed. FIG. 8 is a sectional elevation view of the door's lower extreme and the bottom portion of the container. The sliding door is slightly raised in this view. The door's lower extreme forms tang 58, which preferably includes a tapered edge as shown (The edge could also be rounded). The container includes clevis 62, which is positioned to receive tang 58 when the sliding door is fully lowered. The clevis is preferably surrounded and formed by a material which can undergo substantial elastic deformation (such as a pliable plastic or rubber compound). Such a material would not be optimal for forming the balance of the container. Thus, the clevis is preferably made of a different material than the rest of the container. In the embodiment shown, clevis 62 is actually created by a separate insert 60. In order to seal the outer elongate sleeve of the medical bandaging product, a portion of the outer elongate sleeve is passed between tang 58 and clevis 62. The medical material within the sleeve is then pushed back in the box so that only the outer elongate sleeve protrudes through the door. The door is then lowered.

Figure 9:
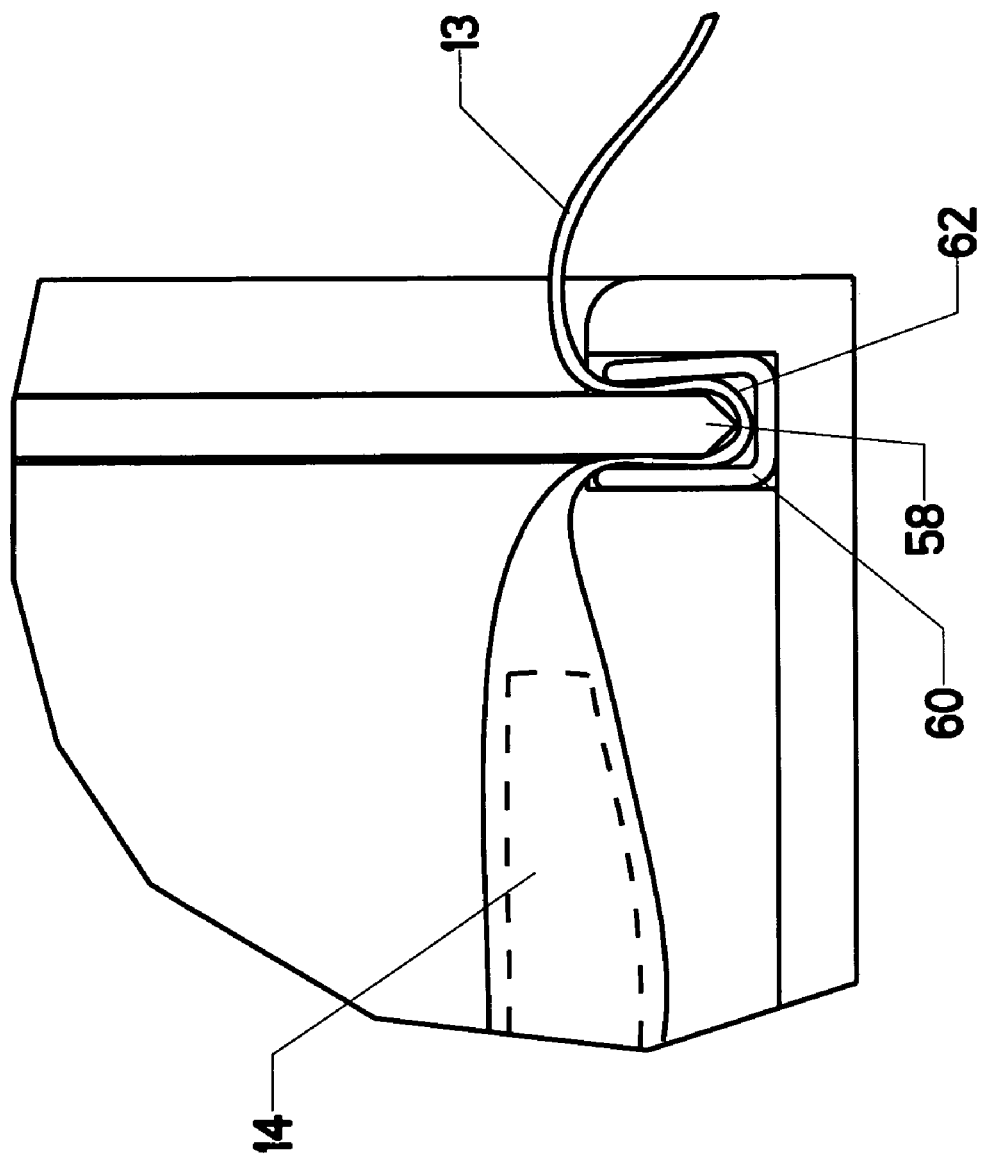
FIG. 9 is a sectional elevation view, showing how the outer elongate sleeve of the medical bandaging product is clamped within the tang and clevis joint.

FIG. 9 shows a sectional view in the same location after tang 58 has pinched outer elongate sleeve 13 into clevis 62. The reader will observe how the insert has plastically deformed in order to bear tightly against the outer elongate sleeve and perfect the seal. Although a rigid material could be used to form the clevis, the pliable nature of the insert provides a better seal and a pliable insert is therefore preferred.

Figure 14:
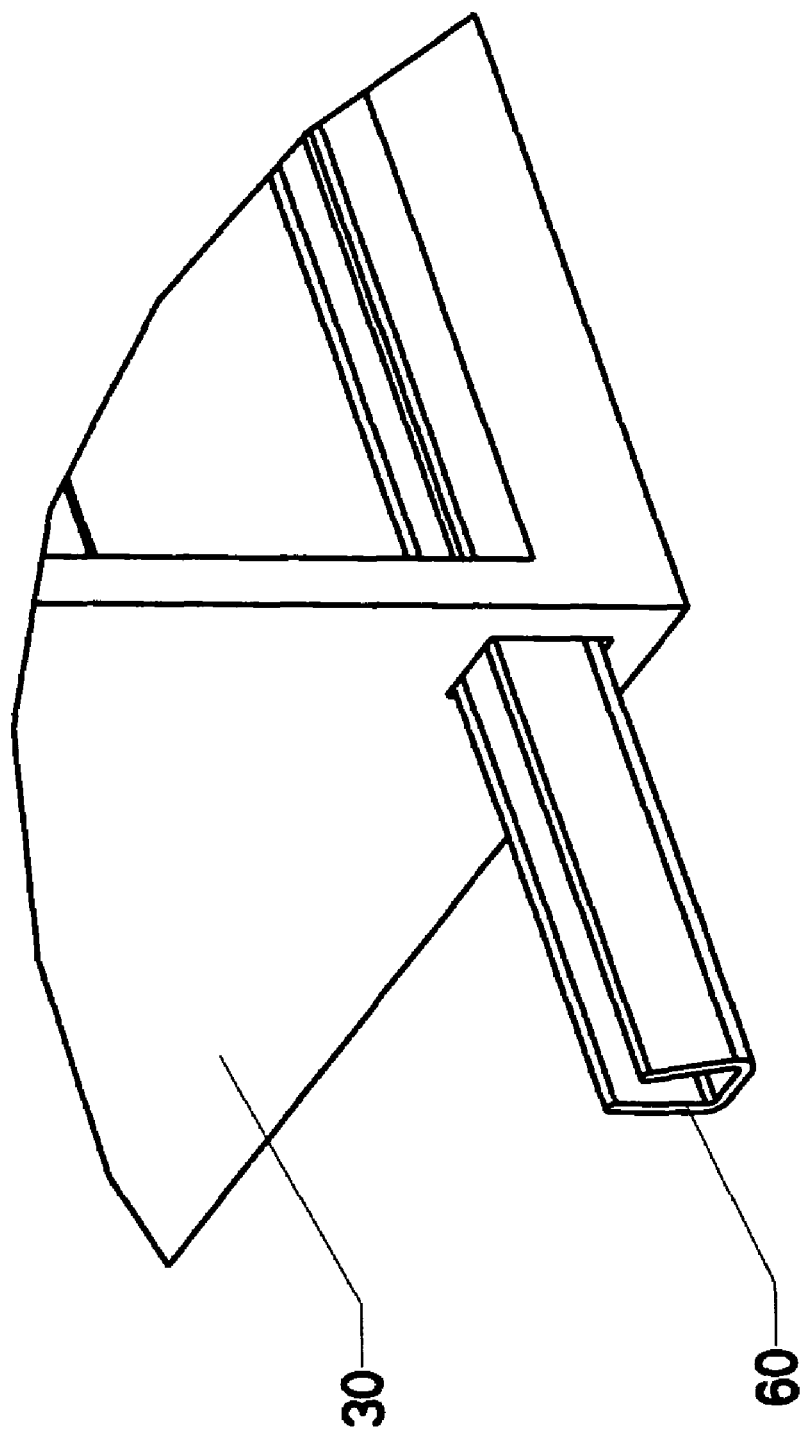
FIG. 14 is a perspective view, showing how the clevis insert can be removed from the dispenser system.

FIG. 14 shows how insert 60 can be pulled free of the dispenser system through opening 70 in the side wall. This allows an old insert to be removed and a fresh one put in its place. Because the insert may become worn, it is preferable to provide such a means for its replacement.

Those skilled in the art will realize that the tang and clevis joint formed between the door and the container can assume a variety of forms. As an example, it is possible to place the clevis on the bottom of the door and configure this clevis to close over a tang extending upward from the bottom of the box. However, since it is convenient to form the tang on the door, the embodiment shown is preferred.

Returning again to FIG. 6, another preferred feature of the invention will be described. Indicator panel 54 is included on the outward facing side of the sliding door. When the door is open, it is plainly visible. However, when the door is fully closed, indicator panel 54 is covered by occluding panel 72. While the indicator panel can assume many forms, one good approach is to use a brightly colored strip (such as a red strip). When the red strip is visible, the user immediately knows that the door is at least partially open. This feature helps ensure that the medical bandaging product is fully resealed.

Figure 10:
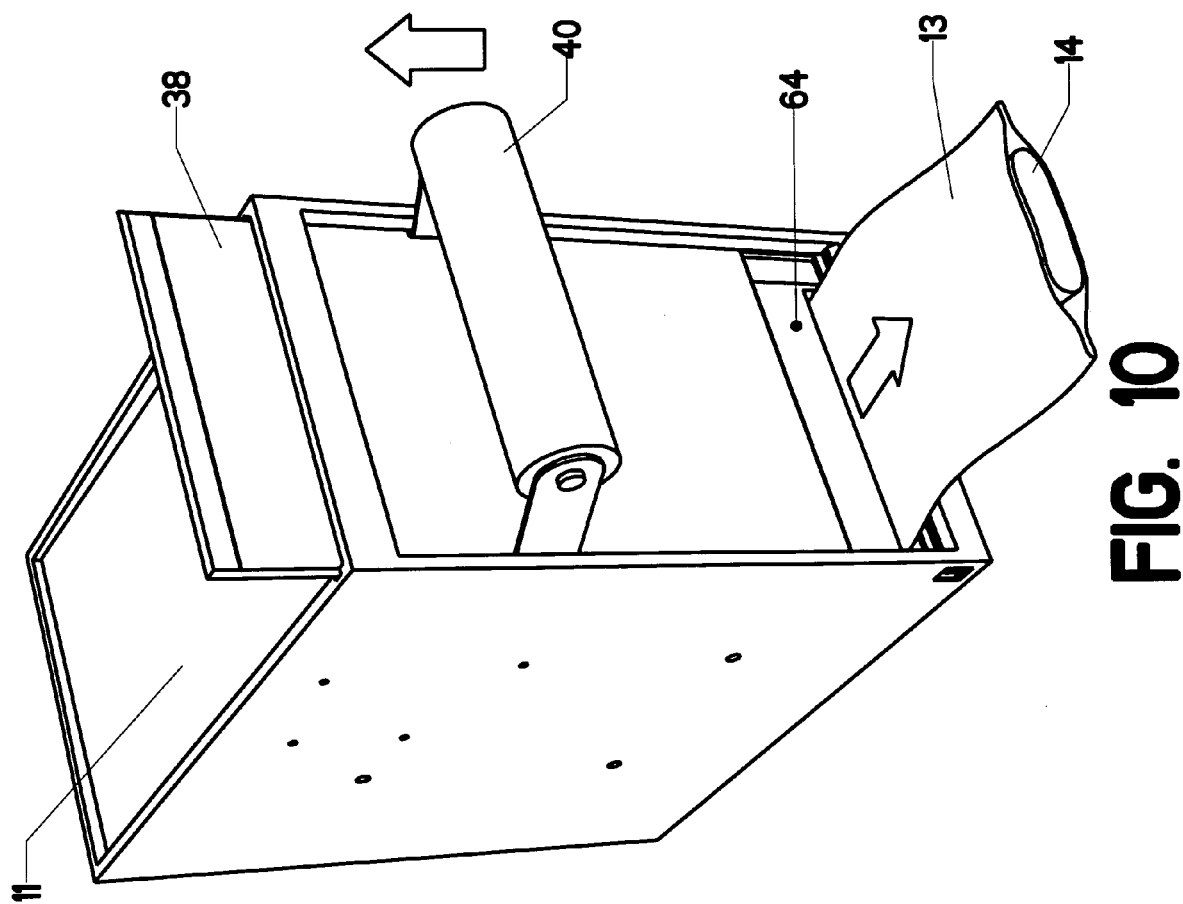
FIG. 10 is a perspective view, showing the dispensing of a length of medical bandaging product through the dispensing opening.
Figure 11:
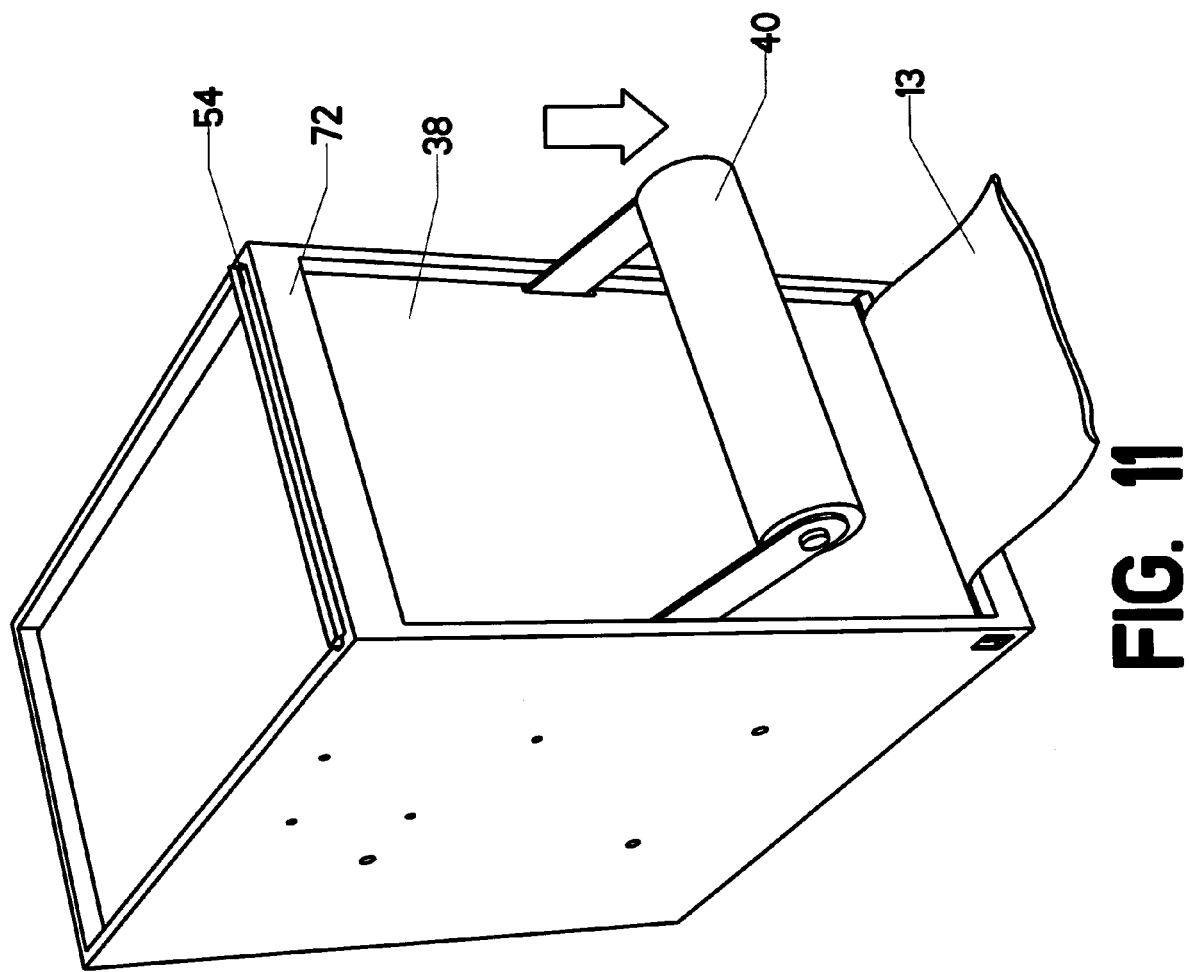
FIG. 11 is a perspective view, showing how the indicator bar indicates that the sliding door is not completely closed.

FIGS. 10-11 illustrate the operation of this feature. In FIG. 10, dispenser 11 (which is a prior art cardboard box containing a roll of medical material) has been loaded into the container. The user raises handle 40 in order to raise sliding door 38 and create dispensing opening 64. The user then pulls a desired length of medical bandaging product 10 through the dispensing opening. The user then cuts the desired length free of the roll—using a pair of scissors or a knife. The result will be a short length of bandaging product protruding through the dispensing opening. The user then pushes the medical material back into the container (back down inside the outer elongate sleeve), leaving only the outer elongate sleeve protruding through the opening. The user then presses down on the handle to close the sliding door onto the severed end of the outer elongate sleeve.

FIG. 11 shows this operation when the sliding door is down but not fully seated. The reader will observe that a small portion of indicator panel 54 protrudes up beyond occluding panel 72. If a red strip is used as the indicator panel, the user will be able to see a portion of the red strip. The user therefore immediately knows that the door is not fully seated and presses the handle further down until the door is fully seated. The elongate sleeve of the medical bandaging product is thereby tightly sealed. The door is left in the closed position until the user again desires to withdraw a length of the medical bandaging product. The sealing interface provided by the tang and clevis ensure that moisture will not invade the elongate sleeve and cause the material inside to harden.

Those skilled in the art will realize that the indicator and occluding panels could assume various forms that differ from the illustrated embodiment. As an example, the indicator panel could be placed on the forward facing surface of the dispenser box. The occluding panel could then be an opaque portion of the door that slides over the indicator panel when the door is fully seated.

As mentioned previously, the medical bandaging products are manufactured in differing widths. Most products are available in 1 inch, 2 inch, 3 inch, 4 inch, 5 inch, and 6 inch widths. Thus, it is desirable to provide dispenser systems in differing widths as well. A 3 inch wide dispenser system can handle bandaging products between 1 and 3 inches wide. A 6 inch wide dispenser system can handle bandaging products between 5 and 6 inches wide. Alternatively, a box configured to handle each specific bandage width can be provided as well.

FIG. 12 shows two dispenser systems 26 of differing widths. The left hand box is four inches wide while the right hand box is 6 inches wide. The boxes will customarily be placed next to each other on a shelf, table, or cart. It may be helpful to link the boxes together. Accordingly, linking features are provided on the sides of the boxes. For the particular embodiment shown, each side has a set of corresponding mounting holes 46.

Figure 13:
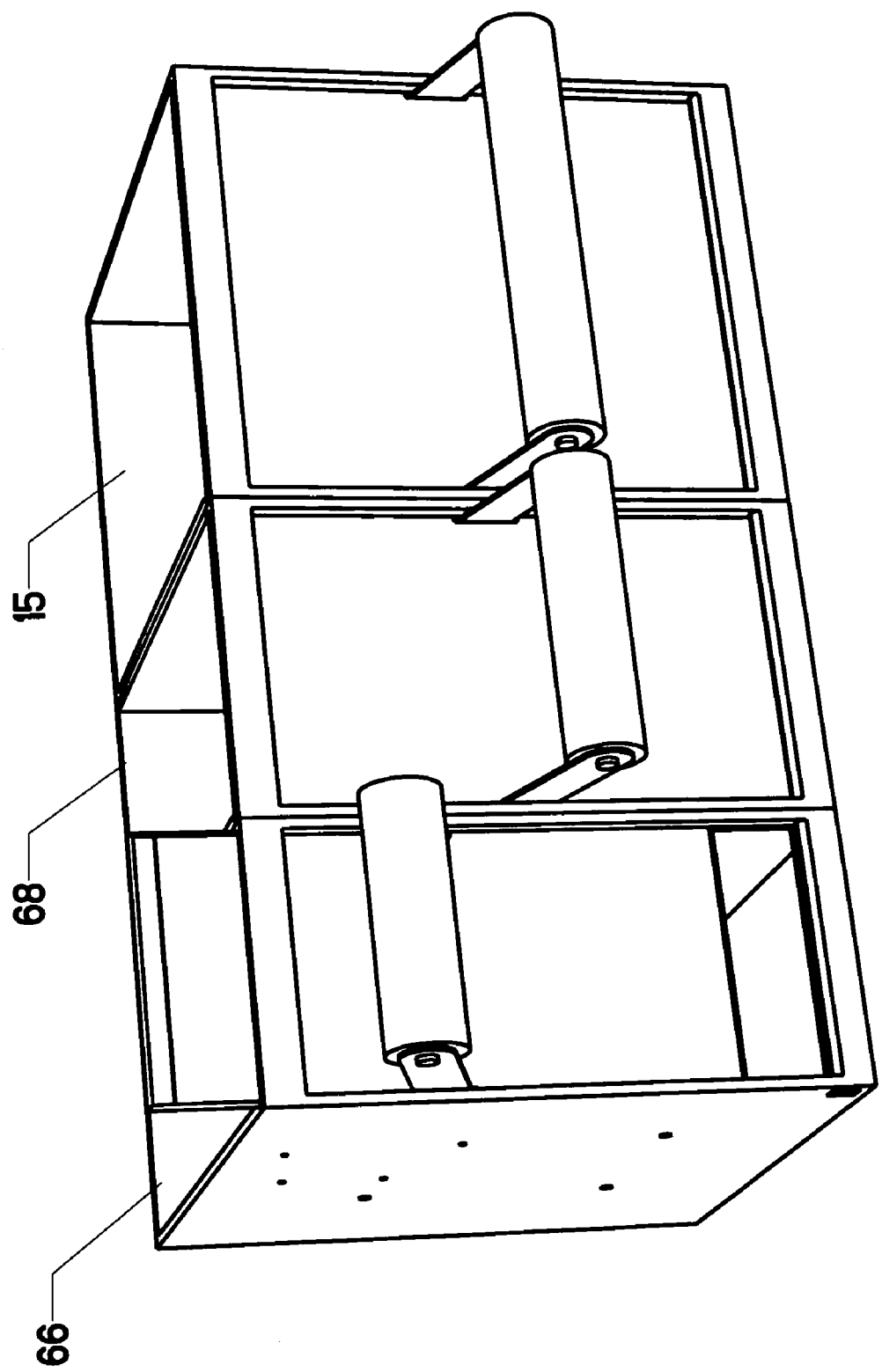
FIG. 13 is a perspective view, showing three dispenser systems of differing widths linked together.

When the dispenser systems are placed side by side, fasteners can be placed through the aligned mounting holes to lock the boxes together. FIG. 13 shows an assembly of three boxes made by placing fasteners in the aligned linking holes. 3 inch box 66, 4 inch box 68, and 6 inch box 15 have joined together.

Returning now to FIG. 5, several additional features will be described. It may be desirable to attach a cutting device—such as a pair of scissors—to the dispenser system. Cutting device mount 74 is a hole positioned to receive a piece of attachment hardware. Many well known attachment devices could be used. One good example is the use of a chain or cord attached to a threaded stud. The threaded stud could be attached to cutting device mount 74. The free end of the chain would then be attached to the scissors. In addition, a bracket can be provided to hold the scissors themselves.

It may also be desirable to attach a water dispensing device. As explained previously, once the moisture-activated medical material is removed from the outer elongate sleeve, it is customarily wetted prior to application. Thus, it may be convenient to attach a water dispensing device to the dispenser system. One good example would be a water bottle with a dispensing valve proximate its lower extreme (such as the type used to dispense liquor from inverted liquor bottles in a bar). Water dispenser mount 76 comprises two holes positioned to provide a mounting point for a water bottle bracket or similar item.

Some users may wish to mount the cutting device and/or water dispenser on the left side of the dispenser system, while other users may wish to mount these items on the right side. The mounting points shown in FIG. 5 are for mounting the hardware on the left side. A corresponding set of holes is provided on the right side of the dispenser system. The ability to select the desired side to mount the hardware is particularly helpful when several dispenser systems are linked together—such as shown in FIG. 13.

Figure 16:
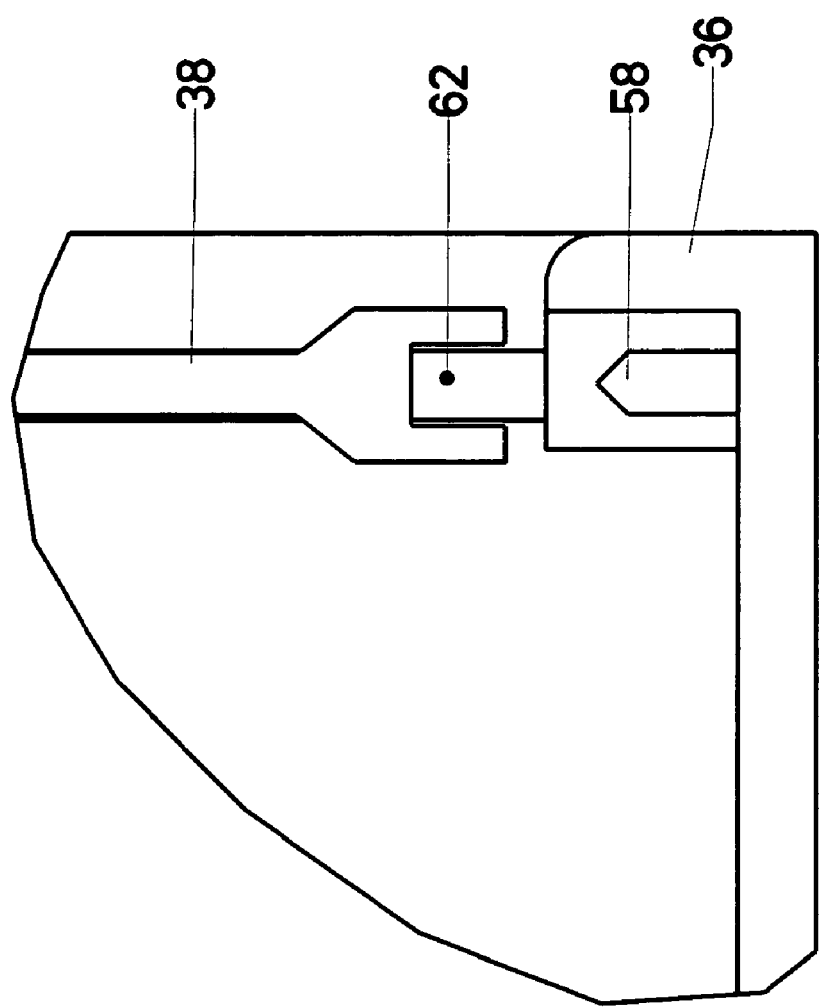
FIG. 16 is a sectional elevation view, showing an alternate embodiment in which the clevis is placed on the bottom of the door and the tang is stationary.

FIG. 16 illustrates the alternate embodiment in which the clevis is placed on the bottom of the door and the tang extends upward from the bottom of the box. The reader will observe how the bottom of sliding door 38 opens to form clevis 62, which is positioned to close over tang 58.

Figure 15:
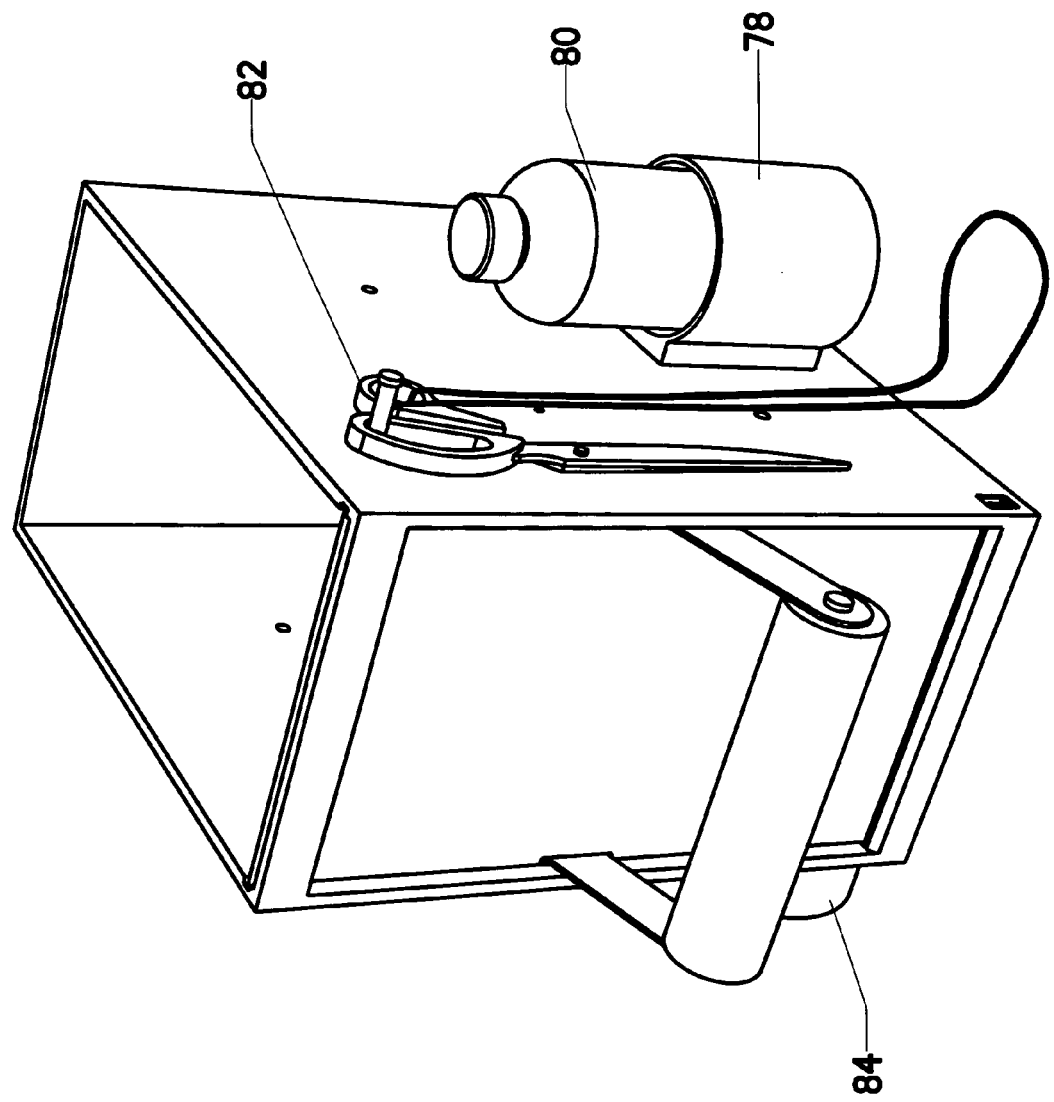
FIG. 15 is a perspective view, showing how a water bottle and other items can be attached to the side of the dispenser system.

FIG. 15 shows a dispenser system with a cutting device and a water bottle attached. Scissors 82 have been attached by a threaded stud placed in the cutting device mount. A cord links the scissors to the threaded stud so they will not be misplaced. Bottle holder 78 has been attached to water dispenser mount 76. Water bottle 80 is placed within the bottle holder. Additional attachment features can be provides, such as an attachment point for holding measuring tape 84.

A strip-type medical bandaging product having an outer elongate sleeve has been illustrated throughout this disclosure. However, the reader should bear in mind that other types of moisture-activated medical bandaging products exist. As an example, some products have a foil seal box incorporating a protruding lip—with an opening—through which the bandaging material is fed from the box. The presently-disclosed dispenser system would work for these products as well. The protruding lip would be placed in the dispensing opening and the sliding door would then be used to seal the protruding lip.

Although the preceding description contains significant detail, it should not be viewed as limiting the invention but instead as providing illustrations of the preferred embodiments of the invention. As an example, the connection between the levers and the sliding door could be made by providing horizontal pins on the door which rest in elongated slots on the handles. The functional interaction between the levers and the door would be the same. Many other alterations could be made to the embodiments illustrated without altering the substance of the invention. Thus, the scope of the present invention should thus be defined by the following claims rather than any specific examples given.

Having described our invention, we claim:

1. A dispenser system for dispensing a desired portion from a moisture-activated medical bandaging product having an outer seal, then resealing a remaining portion of said product remaining within said dispenser system, comprising:
   a. an enclosure having a front opening;
   b. a sliding door, having a lower extreme, slidably disposed within said front opening;
   c. wherein said sliding door is movable to a raised position wherein a dispensing opening is formed between said lower extreme and said enclosure, so that said portion of moisture-activated medical bandaging product can be drawn through said dispensing opening;
   d. wherein said sliding door is movable to a lowered position wherein said dispensing opening is closed;
   e. a tang and clevis interface formed proximate said lower extreme of said door when said door is moved to said lowered position;
   f. wherein said tang and clevis interface is positioned so that when said sliding door is moved to said lowered position, said outer seal of said medical bandaging product is forced into said tang and clevis interface, thereby forming a seal;
   g. wherein said sliding door is raised and lowered by a handle; and h. wherein said handle includes at least one lever pivotally connected to said enclosure, wherein said at least one lever bears against said sliding door and provides a mechanical advantage.

2. A dispenser system as recited in claim 1, wherein said sliding door includes at least one lever relief slot, and wherein said at least one lever lies within said lever relief slot and moves said sliding door by bearing against the boundaries of said at least one lever relief slot.

3. A dispenser system as recited in claim 1, wherein said handle includes a soft covering.

4. A dispenser system as recited in claim 2, wherein said handle includes a soft covering.

5. A dispenser system as recited in claim 1, wherein:
   a. said sliding door includes an indicator panel; and
   b. said enclosure includes an occluding panel which is positioned to cover said indicator panel when said door is in said lowered position.

6. A dispenser system as recited in claim 5, wherein:
   a. said sliding door includes a top side; and
   b. said indicator panel is located proximate said top side of said sliding door.

7. A dispenser system as recited in claim 1, wherein:
   a. said enclosure includes a right groove and a left groove;
   b. said sliding door includes a right side and a left side;
   c. said right side of said sliding door slides within said right groove; and
   d. said left side of said sliding door slides within said left groove.

8. A dispenser system as recited in claim 2, wherein:
   a. said enclosure includes a right groove and a left groove;
   b. said sliding door includes a right side and a left side;
   c. said right side of said sliding door slides within said right groove; and
   d. said left side of said sliding door slides within said left groove.

9. A dispenser system as recited in claim 1, wherein said lower extreme of said sliding door is pointed.

10. A dispenser system as recited in claim 1, wherein a portion of said sliding door is transparent.

11. A dispenser system as recited in claim 1, wherein:
    a. said tang and clevis interface is formed by a tang on said lower extreme of said door and a clevis connected to said enclosure;
    b. said enclosure is made of a first material and said clevis is made of a second material.

12. A dispenser system as recited in claim 11, wherein said clevis is made of a pliable material which is able to undergo substantial elastic deformation.

13. A dispenser system as recited in claim 1 wherein said clevis is removable from said dispenser system.

14. A dispenser system as recited in claim 1, wherein:
    a. said enclosure has a left side and a right side;
    b. said left side has attachment features for joining said enclosure to a right side of a second adjacent enclosure; and
    c. said right side has attachment features for joining said enclosure to a left side of a second adjacent enclosure.

15. A dispenser system as recited in claim 1, further comprising a mounting point for a water dispenser.

16. A dispenser system as recited in claim 1, further comprising a mounting point for a cutting device.

17. A dispenser system as recited in claim 1, wherein said clevis is removable from said dispenser system.

18. A dispenser system as recited in claim 2, wherein:
    a. said sliding door includes an occluding panel; and
    b. said dispenser system includes an indicator panel positioned to be occluded by said occluding panel when said door is in said lowered position.

19. A dispenser system as recited in claim 1, wherein said lower extreme of said sliding door is rounded.

20. A dispenser system for dispensing a desired portion from a moisture-activated medical bandaging product having an outer seal, then resealing a remaining portion of said product remaining within said outer seal, comprising:
    a. an enclosure having a front opening;
    b. a sliding door, having a lower extreme, slidably disposed within said front opening;
    c. wherein said sliding door is movable between a raised position wherein a dispensing opening is formed between said lower extreme and said enclosure, so that said portion of moisture-activated medical bandaging product can be drawn through said dispensing opening, and a closed position wherein said dispensing opening is closed;
    d. a tang on said lower extreme of said door;
    e. a clevis positioned to receive said tang when said door is in said closed position; and
    f. at least one lever movably connected to said enclosure and said sliding door so that said at least one lever provides a mechanical advantage in moving said door.

21. A dispenser system for dispensing a desired portion from a moisture-activated medical bandaging product having an outer seal, then resealing a remaining portion of said product remaining within said outer seal, comprising:
    a. an enclosure having a front opening;
    b. a sliding door, having a lower extreme, slidably disposed within said front opening;
    c. wherein said sliding door is movable between a raised position wherein a dispensing opening is formed between said lower extreme and said enclosure, so that said portion of moisture-activated medical bandaging product can be drawn through said dispensing opening, and a closed position wherein said dispensing opening is closed;
    d. a clevis on said lower extreme of said door;
    e. a tang positioned to slide into said clevis when said door is in said closed position; and
    f. at least one lever movably connected to said enclosure and said sliding door so that said at least one lever provides a mechanical advantage in moving said door.

* * * * *